United States Patent [19]

Smithwick, Jr. et al.

[11] 4,199,499
[45] Apr. 22, 1980

[54] PHARMACOLOGICALLY ACTIVE PEPTIDES

[75] Inventors: Edward L. Smithwick, Jr.; Robert C. A. Frederickson, both of Indianapolis; Robert T. Shuman, Greenwood, all of Ind.

[73] Assignee: Eli Lilly and Company, Indianapolis, Ind.

[21] Appl. No.: 936,437

[22] Filed: Aug. 24, 1978

[51] Int. Cl.² .................... C07C 103/52; A61K 37/00
[52] U.S. Cl. .............................. 260/112.5 R; 424/177
[58] Field of Search .................. 260/112.5 R; 424/177

[56] References Cited

U.S. PATENT DOCUMENTS

| | | | |
|---|---|---|---|
| 4,028,319 | 6/1977 | Jones, Jr. et al. | 260/112.5 R |
| 4,075,190 | 2/1978 | Sarantakis | 260/112.5 R |
| 4,092,304 | 5/1978 | Jones, Jr. et al. | 260/112.5 R |
| 4,103,005 | 7/1978 | Li | 260/112.5 R |

*Primary Examiner*—Delbert R. Phillips
*Attorney, Agent, or Firm*—William C. Martens, Jr.; Arthur R. Whale

[57] ABSTRACT

Compounds of the formula

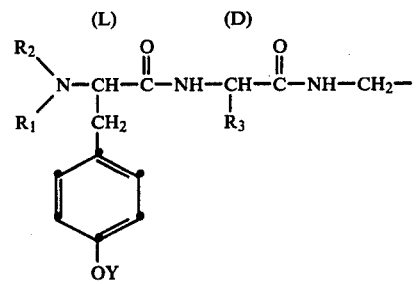

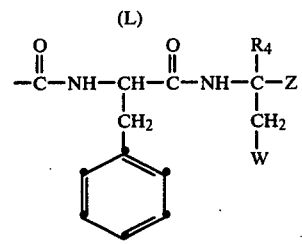

and pharmaceutically acceptable non-toxic acid addition salts thereof, in which L and D define the chirality;

$R_1$ and $R_2$ independently are hydrogen or $C_1$–$C_3$ primary alkyl;

$R_3$ is $C_1$–$C_4$ primary or secondary alkyl, $C_1$–$C_2$ hydroxyalkyl, or —$CH_2CH_2$—U—$CH_3$, in which U is O or S;

$R_4$ is $C_1$–$C_3$ primary alkyl;

Y is hydrogen or acetyl;

Z is —$CH_2OH$ or

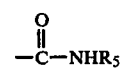

in which $R_5$ is $C_1$–$C_3$ alkyl or hydrogen; and W is isopropyl, —$VR_6$, or —$CH_2$—X—$CH_3$, in which V is O or S, $R_6$ is $C_1$–$C_4$ alkyl or aralkyl, and X is O, S, or $CH_2$—; are useful analgesic agents.

65 Claims, No Drawings

PHARMACOLOGICALLY ACTIVE PEPTIDES

BACKGROUND OF THE INVENTION

This invention relates to a novel class of compounds which exhibit analgesic activity upon parenteral administration.

Recently, endogenous substances having morphine-like properties have been extracted from mammalian brain or csf. These substances, named enkephalin, have been identified by Hughes et al., *Nature*, 258, 577 (1975) as pentapeptides having the following sequences:

H-Tyr-Gly-Gly-Phe-Met-OH
H-Tyr-Gly-Gly-Phe-Leu-OH.

These compounds are referred to as methionine-enkephalin and leucine-enkephalin, respectively.

Although these compounds have been shown to exhibit analgesic activity in mice upon administration intracerebroventricularly [Buscher et al., *Nature*, 261, 423 (1976)], they are practically devoid of any useful analgesic activity when administered parenterally.

Since the discovery of the enkephalins, much effort has been devoted to preparing analogs of the enkephalins in the hope of finding compounds having enhanced activity and practical utility due to their bioavailability by parenteral or oral administration.

Dutta et al., *Life Sciences* 21, pp. 559–562 (1977) report certain structure modifications which, they suggest, tend to enhance potency. They suggest activity can be enhanced by any or all of the following:

(a) substitution of Gly in position 2 by certain D- or α-aza-amino acids;

(b) conversion of the terminal carboxyl by esterification to the methyl ester or the amide;

(c) modification of the Phe in the 4-position by α-aza substitution, N-methylation, or hydrogenation of the aromatic ring.

In addition, Roemer et al., *Nature* 268, pp. 547–549 (1977), suggest modification of the $Met^5$ to its corresponding carbinol and oxidation of the Met sulfur to the sulfoxide as useful modifications.

Another structural modification of significance is that reported in Belgian Pat. No. 859,026. This publication suggests enhancement of activity and bioavailability of enkephalin analogs by insertion of a D-amino acid residue in position 2, conversion of the terminal carboxyl to an amide, and N-alkylation of the amino acid residue in position 5.

A further novel class of compounds has now been discovered. These compounds exhibit significant and demonstrable analgesic activity when administered systemically. The compounds also are useful in the amelioration of emotional disease. It is to this class of compounds that this invention is directed.

SUMMARY OF THE INVENTION

Thus, this invention relates to a class of compounds having the formula and pharmaceutically acceptable non-toxic acid addition salts thereof, in which L and D define the chirality;

$R_1$ and $R_2$ independently are hydrogen or $C_1$–$C_3$ primary alkyl;

$R_3$ is $C_1$–$C_4$ primary or secondary alkyl, $C_1$–$C_2$ hydroxyalkyl, or —$CH_2CH_2$—U—$CH_3$, in which U is O or S;

$R_4$ is $C_1$–$C_3$ primary alkyl;

Y is hydrogen or acetyl;

Z is —$CH_2OH$ or $$-\overset{O}{\underset{\|}{C}}-NHR_5$$

in which $R_5$ is $C_1$–$C_3$ alkyl or hydrogen; and W is isopropyl, —$VR_6$, or —$CH_2$—X—$CH_3$, in which V is O or S, $R_6$ is $C_1$–$C_4$ alkyl or aralkyl, and X is O, S, or —$CH_2$—.

A preferred class of compounds is that class in which W is —$CH_2$—X—$CH_3$, and, of this class, those compounds in which X is sulfur.

DETAILED DESCRIPTION OF THE INVENTION

As indicated above, the compounds of this invention have the following structure:

Also included are the pharmaceutically acceptable non-toxic acid addition salts of these compounds.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salts are those prepared from hydrochloric acid, acetic acid, or succinic acid. Any of the above salts are prepared by conventional methods.

As will be noted from the definition of the various substituents which appear in the above structure, the compounds which are defined by this structure are unsubstituted or N-substituted amides of pentapeptides or primary alcohol derivatives of such pentapeptides.

The stereoconfiguration of the compounds of this invention is an essential feature thereof. For the sake of convenience, the amino acid residues of the modified pentapeptides of this invention are numbered sequentially beginning with the residue at the terminal amino function. The chirality of the amino acid residues, reading from Position 1 through Position 4, is L, D, none, and L. The residue in Position 3 is a glycine moiety, and, thus, no chirality as to this residue exists. As to Position 5 (the C-terminal position) which is a primary or secondary amide or a primary alcohol, its chirality is defined as that which is consistent with and corresponds to the corresponding putative L-amino acid residue, the corresponding putative D-amino acid residue, or the racemic mixture of both.

The group $R_5$ as used herein is defined to include the group "$C_1$-$C_3$ alkyl". By the term "$C_1$-$C_3$ alkyl" is intended methyl, ethyl, n-propyl and isopropyl.

The groups $R_1$, $R_2$, and $R_4$ as used herein are defined to include the group "$C_1$-$C_3$ primary alkyl". By the term "$C_1$-$C_3$ primary alkyl" is intended methyl, ethyl, and n-propyl.

The group $R_3$ appearing in the above structural formula is defined to include the group "$C_1$-$C_4$ primary or secondary alkyl". By the term "$C_1$-$C_4$ primary or secondary alkyl" is meant methyl, ethyl, n-propyl, isopropyl, n-butyl, isobutyl, and sec-butyl.

The group $R_3$ is also defined as "$C_1$-$C_2$ hydroxyalkyl". By the term "$C_1$-$C_2$ hydroxyalkyl" is meant hydroxymethyl, 1-hydroxyethyl, and 2-hydroxyethyl.

The group $R_6$ as used herein is defined to include the groups "$C_1$-$C_4$ alkyl" and "aralkyl". By the term "$C_1$-$C_4$ alkyl" is meant methyl, ethyl, n-propyl, isopropyl, n-butyl, isobutyl, sec-butyl, and t-butyl. Preferably, $R_6$, when it is $C_1$-$C_4$ alkyl, is ethyl. By the term "aralkyl" is meant unsubstituted and substituted aralkyls and preferably is directed to those aralkyl groups having from about 7 to about 10 carbon atoms. More preferably, the aralkyl group is benzyl or substituted benzyl. Typical substituents include halo, such as fluoro, chloro, or bromo; $C_1$-$C_3$ alkoxy, such methoxy, ethoxy, or propoxy; trifluoromethyl; $C_1$-$C_3$ alkyl; and $C_1$-$C_3$ alkylthio, such as methylthio, ethylthio, and the like. Preferably, the substituent, when one is present, is located in the para position. A highly preferred substituent is methoxy, and highly preferred aralkyl group is p-methoxybenzyl.

With respect to the particular position residues of the modified pentapeptides of this invention, the following considerations prevail:

(A). Position 1.

This position represents the amino-terminal portion of the peptide. The residue is that which results from L-tyrosine or L-(O-acetyl)tyrosine. In either instance, the residue can be N-unsubstituted, in which case both $R_1$ and $R_2$ are hydrogen. Moreover, the residue can be substituted by one or two $C_1$-$C_3$ primary alkyl groups, in which case $R_1$ and/or $R_2$ is $C_1$-$C_3$ primary alkyl. Specific illustrations of $C_1$-$C_3$ primary alkyl substitution include N-methyl-, N-ethyl-, N-n-propyl-, N,N-dimethyl, N,N-diethyl, N,N-di-n-propyl, N-methyl-N-ethyl, N-methyl-N-n-propyl, N-ethyl-N-n-propyl, and the like. Preferably, the tyrosyl or O-acetyltyrosyl residue which is present in Position 1 of the peptide of this invention is N-unsubstituted. Furthermore, it is preferred that the residue is tyrosyl.

(b). Position 2.

The amino acid residue which is present in the second position of the peptide of this invention must be the D stereoisomer and is any of several amino acid residues. These include residues derived from D-alanine (Ala) ($R_3$ is methyl), D-α-aminobutyric acid (Abu) ($R_3$ is ethyl), D-norvaline (Nva) ($R_3$ is n-propyl), D-valine (Val) ($R_3$ is isopropyl), D-norleucine (Nle) ($R_3$ is n-butyl), D-leucine (Leu) ($R_3$ is isobutyl), D-isoleucine (Ile) ($R_3$ is sec-butyl), D-methionine (Met) ($R_3$ is 2-methylthioethyl), D-serine (Ser) ($R_3$ is hydroxymethyl), D-threonine (Thr) ($R_3$ is 1-hydroxyethyl), D-homoserine (Hse) ($R_3$ is 2-hydroxyethyl), and D-(O-methyl)-homoserine [Hse(Me)] ($R_3$ is 2-methoxyethyl). Preferably, $R_3$ is $C_1$-$C_4$ primary alkyl, and, more preferably, $R_3$ is methyl, i.e., the residue is that derived from D-alanine.

(C). Position 3.

The amino acid residue present in this position is that derived from glycine (Gly).

(D). Position 4.

The amino acid residue present in this position is that derived from L-phenylalanine (Phe).

(E). Position 5.

The residue present in the C-terminal position of the compounds of this invention is an α-carbon substituted amino acid structurally derivatized to its amide (Z is

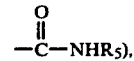

or its primary alcohol (Z is —CH$_2$OH). The chirality of the amino acid residue in Position 5 of the pentapeptide is the L-, D-, or the D,L- mixture. The residue is represented by any of the following, each of which has been substituted at the α-carbon and derivatized to its amide or primary alcohol. These include methionine (Met) (W is —CH$_2$SCH$_3$), norleucine (Nle) (W is —CH$_2$CH$_2$CH$_3$), (O-methyl)homoserine [Hse(Me)] (W is —CH$_2$OCH$_3$), leucine (Leu) [W is —CH(CH$_3$)$_2$], (O-alkyl or O-aralkyl)serine [Ser(Alk) or Ser(Aralk)] (W is OR$_6$), or (S-alkyl or S-aralkyl)cysteine [Cys(Alk) or Cys(Aralk)] (W is SR$_6$). Specific examples of the group W are methylthiomethyl, n-propyl, methoxymethyl, isopropyl, methoxy, ethoxy, n-propoxy, benzyloxy, p-methoxybenzyloxy, m-chlorobenzyloxy, o-trifluoromethylbenzyloxy, m-ethoxybenzyloxy, methylthio, ethylthio, isopropylthio, n-butylthio, benzylthio, p-methoxybenzylthio, o-bromobenzylthio, p-ethylthiobenzylthio, p-methylbenzylthio, and the like. Preferably, the residue in Position 5 is a structural derivative of methionine. In those instances in which the residue in Position 5 is O-substituted serine or S-substituted cysteine, it is preferred, when the substituent is a $C_1$–$C_4$ alkyl, that it is ethyl and, when it is aralkyl, that it is p-methoxybenzyl.

The residue in Position 5 is substituted ($R_4$) at its α-carbon by a $C_1$–$C_3$ primary alkyl group. The represented substituents are methyl, ethyl, and n-propyl. Preferably, the α-carbon substituent is methyl.

In addition, the residue in Position 5 is an amide or a primary alcohol. Preferably, the residue is an amide, and, more preferably, a primary amide, i.e., $R_5$ is hydrogen. When the amide is a secondary amide, $R_5$ is a $C_1$–$C_3$ alkyl group. In those instances, the terminal amide group is N-methyl, N-ethyl, N-n-propyl, or N-isopropyl.

In this specification, the following abbreviations, most of which are well known and are commonly used in the art, are employed:

Abu—α-aminobutyric acid
Ala—alanine
Cys—cysteine
Gly—glycine
Hse—homoserine
Ile—isoleucine
Leu—leucine
Met—methionine
Nle—norleucine
Nva—norvaline
Phe—phenylalanine
Ser—serine
Thr—threonine
Tyr—tyrosine
Val—valine
Ac—acetyl
Me—methyl
Et—ethyl
Ip—isopropyl
Pr—n-propyl
Bu—n-butyl
i-Bu—isobutyl
t-Bu—t-butyl
s-Bu—sec-butyl
BOC—t-butyloxycarbonyl
Bzl—benzyl
DCC—N,N'-dicyclohexylcarbodiimide
HBT—1-hydroxybenzotriazole
DMF—N,N-dimethylformamide
TFA—trifluoroacetic acid
THF—tetrahydrofuran
DEAE—diethylaminoethyl Examples of typical compounds of this invention include the following:

H-L-Tyr-D-Ala-Gly-L-Phe-D,L-(α-Me)Met-NH₂;
H-L-Tyr-D-Met-Gly-L-Phe-D,L-(α-Me)Met-NH₂;
H-L-Tyr-D-Ser-Gly-L-Phe-L-(α-Me)Met-NH₂;
H-L-Tyr-D-Abu-Gly-L-Phe-L-(α-Et)Met-NH₂;
H-L-Tyr-D-Thr-Gly-L-Phe-D-(α-Me)Met-NH₂;
H-L-Tyr-D-Nva-Gly-L-Phe-L-(α-Me)Met-NH₂;
H-L-Tyr-D-Val-Gly-L-Phe-L-(α-Me)Met-NH₂;
H-L-Tyr-D-Hse-Gly-L-Phe-D,L-(α-Pr)Met-NH₂;
H-L-Tyr-D-Nle-Gly-L-Phe-(α-Me)Met-NH₂;
H-L-Tyr-D-Nle-Gly-L-Phe-L-(α-Et)Met-NH₂;
H-L-Tyr-D-Leu-Gly-L-Phe-L-(α-Me)Met-NH₂;
H-L-Tyr-D-Hse(Me)-Gly-L-Phe-L-(α-Pr)Met-NH₂;
H-L-Tyr-D-Ile-Gly-L-Phe-L-(α-Me)Met-NH₂;
H-L-Tyr-D-Ile-Gly-L-Phe-L-(α-Pr)Met-NH₂;
H-L-Tyr-D-Ala-Gly-L-Phe-L-(α-Et)Met-NH₂;
H-L-Tyr-D-Ser-Gly-L-Phe-L-(α-Pr)Met-NH₂;
H-L-Tyr-D-Ala-Gly-L-Phe-L-(α-Pr)Met-NH₂;
H-L-Tyr-D-Ala-Gly-L-Phe-L-(α-Me)Met-CH₂OH;
H-L-Tyr-D-Ala-Gly-L-Phe-L-(α-Et)Met-CH₂OH;
H-L-Tyr-D-Ala-Gly-L-Phe-L-(α-Me)Met-CH₂OH;
H-L-Tyr-D-Ala-Gly-L-Phe-D-(α-Pr)Met-CH₂OH;
H-L-Tyr-D-Met-Gly-L-Phe-L-(α-Et)Met-CH₂OH;
H-L-Tyr-D-Val-Gly-L-Phe-L-(α-Me)Met-CH₂OH;
H-L-Tyr-D-Leu-Gly-L-Phe-L-(α-Me)Met-CH₂OH;
H-L-Tyr-D-Val-Gly-L-Phe-L-(α-Et)Met-CH₂OH;
H-L-Tyr-D-Leu-Gly-L-Phe-D-(α-Me)Met-CH₂OH;
H-L-Tyr-D-Ala-Gly-L-Phe-D,L-(α-Me)Nle-NH₂;
H-L-Tyr-D-Ala-Gly-L-Phe-L-(α-Me)Hse(Me)-NH₂;
H-L-Tyr-D-Ala-Gly-L-Phe-L-(α-Me)Nle-NH₂;
H-L-Tyr-D-Ala-Gly-L-Phe-L-(α-Me)Hse(Me)-NH₂;
H-L-Tyr-D-Ser-Gly-L-Phe-L-(α-Et)Met-NH₂;
H-L-Tyr-D-Hse-Gly-L-Phe-L-(α-Me)Met-NH₂;
H-L-Tyr-D-Thr-Gly-L-Phe-L-(α-Me)Met-NH₂;
H-L-Tyr-D-Hse(Me)-Gly-L-Phe-L-(α-Me)Met-CH₂OH;
H-L-Tyr-D-Ser-Gly-L-Phe-L-(α-Me)Met-NH₂;
H-L-Tyr-D-Met-Gly-L-Phe-L-(α-Me)Met-CH₂OH;
H-L-Tyr-D-Ser-Gly-L-Phe-L-(α-Me)Nle-CH₂OH;
H-L-Tyr-D-Met-Gly-L-Phe-L-(α-Me)Hse(Me)-NH₂;
H-L-Tyr(Ac)-D-Ala-Gly-L-Phe-D,L-(α-Et)Met-NH₂;
H-L-Tyr(Ac)-D-Ala-Gly-L-Phe-D,L-(α-Me)Met-NH₂;
H-L-Tyr-D-Nle-Gly-L-Phe-D-(α-Me)Met-CH₂OH;
H-L-Tyr-D-Abu-Gly-L-Phe-D-(α-Me)Met-CH₂OH;
(N-Me)-L-Tyr-D-Ala-Gly-L-Phe-D,L-(α-Me)Met-NH₂;
(N,N-Di-Me)-L-Tyr-D-Ala-Gly-L-Phe-D,L-(α-Me)-Met-NH₂;
(N-Pr)-L-Tyr-D-Ala-Gly-L-Phe-D,L-(α-Me)Met-NH₂;
(N-Et)-L-Tyr-D-Abu-Gly-L-Phe-D,L-(α-Et)Nle-NH₂;
(N,N-di-Pr)-L-Tyr-D-Val-Gly-L-Phe-D,L-(α-Me)-Hse(Me)-NH₂;
(N-Pr)-L-Tyr-D-Leu-Gly-L-Phe-D-(α-Me)Met-NH₂;
(N,N-Di-Et)-L-Tyr-D-Abu-Gly-L-Phe-D,L-(α-Et)-Met-NH₂;
(N-Me,N-Et)-L-Tyr(Ac)-D-Nle-Gly-L-Phe-D,L-(α-Me)Met-NH₂;
(N,N-Di-Me)-L-Tyr(Ac)-D-Ile-Gly-L-Phe-L-(α-Pr)-Met-NH₂;
(N-Me)-L-Tyr(Ac)-D-Leu-Gly-L-Phe-L-(α-Et)Nle-NH₂;
(N-Me)-L-Tyr(Ac)-D-Nva-Gly-L-Phe-D-(α-Me)Hse-(Me)-NH₂;
H-L-Tyr-D-Ser-Gly-L-Phe-D,L-(α-Pr)Met-CH₂OH;
H-L-Tyr-D-Thr-Gly-L-Phe-D,L-(α-Me)Met-CH₂OH;
H-L-Tyr-D-Ala-Gly-L-Phe-D,L-(α-Me)Nle-CH₂OH;
H-L-Tyr-D-Hse-Gly-L-Phe-D,L-(α-Me)Hse(Me)-CH₂OH;
H-L-Tyr-D-Ala-Gly-L-Phe-L-(α-Me)Met-NH(Me);
H-L-Tyr-D-Ala-Gly-L-Phe-D,L-(α-Me)Met-NH(Me);
H-L-Tyr-D-Ala-Gly-L-Phe-L-(α-Et)Met-NH(Me);
H-L-Tyr-D-Ala-Gly-L-Phe-D,L-(α-Me)Met-NH(Et);
H-L-Tyr-D-Ala-Gly-L-Phe-D,L-(α-Et)Met-NH(Et);
H-L-Tyr-D-Ala-Gly-L-Phe-D-(α-Me)Nle-NH(Me);
H-L-Tyr-D-Ala-Gly-L-Phe-D-(α-Et)Met-NH(Pr);
H-L-Tyr-D-Ala-Gly-L-Phe-L-(α-Pr)Met-NH(Me);

H-L-Tyr-D-Nle-Gly-L-Phe-D-(α-Me)Met-NH(Pr);
(N,N-Di-Me)-L-Tyr-D-Ala-Gly-L-Phe-L-(α-Me)-Met-NH(Et);
(N,N-Di-Me)-L-Tyr-D-Nle-Gly-L-Phe-D,L-(α-Me)Met-CH$_2$OH;
(N,N-Di-Et)-L-Tyr-D-Nva-Gly-L-Phe-L-(α-Et)Met-NH(Me);
(N-Pr)-L-Tyr-D-Abu-Gly-L-Phe-D,L-(α-Me)Nle-NH(Me);
(N-Me)-L-Tyr-D-Ala-Gly-L-Phe-D,L-(α-Pr)Hse(-Me)-NH(Me);
(N,N-Di-Me)-L-Tyr-D-Val-Gly-L-Phe-L-(α-Me)-Met-NH(Me);
(N,N-Di-Pr)-L-Tyr-D-Ala-Gly-L-Phe-L-(α-Me)-Met-NH(Me);
(N,N-Di-Me)-L-Tyr(Ac)-D-Ala-Gly-L-Phe-D,L-(α-Me)Met-NH(Me);
(N,N-Di-Pr)-L-Tyr(Ac)-D-Val-Gly-L-Phe-D,L-(α-Me)Met-NH(Me);
(N-Pr)-L-Tyr(Ac)-D-Ile-Gly-L-Phe-D,L-(α-Pr)Nle-NH(Et);
(N-Me)-L-Tyr(Ac)-D-Leu-Gly-L-Phe-D,L-(α-Me)Hse(-Me)-NH(Pr);
H-L-Tyr-D-Ala-Gly-L-Phe-D-(α-Me)Ser(Et)-NH$_2$;
H-L-Tyr-D-Ala-Gly-L-Phe-L-(α-Me)Leu-NH$_2$;
H-L-Tyr-D-Abu-Gly-L-Phe-L-(α-Me)Cys(p-methoxy-Bzl)-NH$_2$;
H-L-Tyr-D-Abu-Gly-L-Phe-D,L-(α-Me)Leu-CH$_2$OH;
H-L-Tyr-D-Nva-Gly-L-Phe-D,L-(α-Et)Leu-NH$_2$;
H-L-Tyr-D-Nva-Gly-L-Phe-D,L-(α-Et)Ser(p-methoxy-Bzl)-NH$_2$;
H-L-Tyr-D-Val-Gly-L-Phe-D,L-(α-Me)Leu-NH$_2$;
H-L-Tyr-D-Val-Gly-L-Phe-D,L-(α-Me)Ser(Me)-NH$_2$;
H-L-Tyr-D-Nle-Gly-L-Phe-L-(α-Me)Cys(Me)-NH$_2$;
H-L-Tyr-D-Nle-Gly-L-Phe-D,L-(α-Et)Leu-NH$_2$;
H-L-Tyr-D-Leu-Gly-L-Phe-D,L-(α-Me)Ser(Bzl)-NH$_2$;
H-L-Tyr-D-Leu-Gly-L-Phe-D,L-(α-Pr)Leu-NH$_2$;
H-L-Tyr-D-Ile-Gly-L-Phe-L-(α-Pr)Cys(Bzl)-NH$_2$;
H-L-Tyr-D-Ile-Gly-L-Phe-D-(α-Pr)Leu-CH$_2$OH;
H-L-Tyr-D-Ala-Gly-L-Phe-D,L-(α-Et)Leu-NH$_2$;
H-L-Tyr-D-Ala-Gly-L-Phe-D,L-(α-Pr)Leu-NH$_2$;
H-L-Tyr-D-Ala-Gly-L-Phe-D,L-(α-Pr)Leu-CH$_2$O;
H-L-Tyr-D-Ala-Gly-L-Phe-L-(α-Pr)Ser(Pr)-NH$_2$;
H-L-Tyr-D-Ala-Gly-L-Phe-D-(α-Et)Leu-CH$_2$OH;
H-L-Tyr-D-Ala-Gly-L-Phe-D,L-(α-Me)Ser(Ip)-NH$_2$;
H-L-Tyr-D-Nle-Gly-L-Phe-D,L-(α-Et)Leu-CH$_2$OH;
H-L-Tyr-D-Ala-Gly-L-Phe-D,L-(α-Me)Cys(i-Bu)-NH$_2$;
H-L-Tyr-D-Val-Gly-L-Phe-D,L-(α-Me)Leu-CH$_2$OH;
H-L-Tyr-D-Leu-Gly-L-Phe-D,L-(α-Me)Leu-CH$_2$OH;
H-L-Tyr-D-Val-Gly-L-Phe-L-(α-Et)Leu-CH$_2$OH;
H-L-Tyr-D-Ala-Gly-L-Phe-L-(α-Me)Ser(p-methoxy-Bzl)-NH$_2$;
H-L-Tyr-D-Ala-Gly-L-Phe-D-(α-Pr)Cys(Et)-NH$_2$;
H-L-Tyr-D-Ala-Gly-L-Phe-D-(α-Me)Ser(Et)-NH$_2$;
H-L-Tyr-D-Ala-Gly-L-Phe-D,L-(α-Me)Cys(Et)-NH$_2$;
H-L-Tyr-D-Ala-Gly-L-Phe-D,L-(α-Et)Ser(Et)-CH$_2$OH;
H-L-Tyr-D-Ala-Gly-L-Phe-D,L-(α-Me)Cys(Et)-CH$_2$OH;
H-L-Tyr-D-Ile-Gly-L-Phe-D,L-(α-Me)Ser(p-chloro-Bzl)-NH$_2$;
H-L-Tyr(Ac)-D-Ala-Gly-L-Phe-D,L-(α-Me)Ser(m-trifluoromethyl-Bzl)-NH$_2$;
H-L-Tyr(Ac)-D-Ala-Gly-L-Phe-D,L-(α-Me)Leu-CH$_2$OH;
H-L-Tyr-D-Nle-Gly-L-Phe-D,L-(α-Me)Cys(o-methyl-Bzl)-NH$_2$;
H-L-Tyr-D-Abu-Gly-L-Phe-L-(α-Me)Leu-CH$_2$OH;
(N-Me)-L-Tyr-D-Ala-Gly-L-Phe-D-(α-Pr)Ser(p-methoxy-Bzl)-NH$_2$;
(N,N-Di-Me)-L-Tyr-D-Ala-Gly-L-Phe-D,L-(α-Me)-Leu-CH$_2$OH;
(N-Et)-L-Tyr-D-Abu-Gly-L-Phe-D,L-(α-Et)Leu-NH$_2$;
(N,N-di-Pr)-L-Tyr-D-Val-Gly-L-Phe-D,L-(α-Me)-Leu-NH$_2$;
(N-Pr)-L-Tyr-D-Leu-Gly-L-Phe-D,L-(α-Me)Leu-NH$_2$;
(N,N-Di-Et)-L-Tyr-D-Abu-Gly-L-Phe-D,L-(α-Me)-Leu-NH$_2$;
(N-Me,N-Et)-L-Tyr(Ac)-D-Nle-Gly-L-Phe-D,L-(α-Me)Leu-NH$_2$;
(N,N-Di-Me)-L-Tyr(Ac)-D-Ile-Gly-L-Phe-D,L-(α-Pr)Leu-NH$_2$;
(N-Me)-L-Tyr(Ac)-D-Leu-Gly-L-Phe-L-(α-Et)D,L-Leu-NH$_2$;
(N-Me)-L-Tyr(Ac)-D-Nva-Gly-L-Phe-D,L-(α-Me)-Ser(t-Bu)-NH$_2$;
H-L-Tyr-D-Ala-Gly-L-Phe-L-(α-Et)Ser(s-Bu)-NH$_2$;
H-L-Tyr-D-Abu-Gly-L-Phe-D,L-(α-Me)Leu-NH$_2$;
H-L-Tyr-D-Ala-Gly-L-Phe-D,L-(α-Me)Cys(p-methoxy-Bzl)-NH$_2$;
H-L-Tyr-D-Ala-Gly-L-Phe-D-(α-Me)Ser(Et)-NH$_2$;
H-L-Tyr-D-Ala-Gly-L-Phe-L-(α-Me)Ser(Et)-NH(Me);
H-L-Tyr-D-Ala-Gly-L-Phe-D,L-(α-Me)Leu-NH(Me);
H-L-Tyr-D-Ala-Gly-L-Phe-D,L-(α-Et)Leu-NH(Me);
H-L-Tyr-D-Ala-Gly-L-Phe-D,L-(α-Me)Leu-NH(Et);
H-L-Tyr-D-Ala-Gly-L-Phe-D,L-(α-Et)Leu-NH(Et);
H-L-Tyr-D-Ala-Gly-L-Phe-D,L-(α-Et)Cys(p-bromo-Bzl)-NH(Pr);
H-L-Tyr-D-Ala-Gly-L-Phe-D,L-(α-Pr)Leu-NH(Me);
H-L-Tyr-D-Ala-Gly-L-Phe-L-(α-Me)Cys(Ip)-NH(Pr);
(N,N-Di-Me)-L-Tyr-D-Ala-Gly-L-Phe-D,L-(α-Me)-Leu-NH(Et);
(N,N-Di-Me)-L-Tyr-D-Ala-Gly-L-Phe-D,L-(α-Me)-Leu-NH$_2$;
(N,N-Di-Et)-L-Tyr-D-Ala-Gly-L-Phe-D,L-(α-Et)-Leu-NH(Me);
(N-Pr)-L-Tyr-D-Ala-Gly-L-Phe-D,L-(α-Me)Leu-NH(Me);
(N-Me)-L-Tyr-D-Ala-Gly-L-Phe-D,L-(α-Pr)Ser(Bzl)-NH(Me);
(N,N-Di-Me)-L-Tyr-D-Val-Gly-L-Phe-D,L-(α-Me)-Leu-NH(Me);
(N,N-Di-Pr)-L-Tyr-D-Ala-Gly-L-Phe-D,L-(α-Me)-Leu-NH-(Me);
H-L-Tyr-D-Ala-Gly-L-Phe-D,L-(α-Me)Ser(Pr)-NH(Me);
(N,N-Di-Me)-L-Tyr(Ac)-D-Ala-Gly-L-Phe-D,L-(α-Me)Leu-NH(Me);

(N,N-Di-Pr)-L-Tyr(Ac)-D-Val-Gly-L-Phe-D,L-(α-Me)Leu-NH(Me);
(N-Pr)-L-Tyr(Ac)-D-Ile-Gly-L-Phe-D,L-(α-Pr)Leu-NH(Et);
(N-Me)-L-Tyr(Ac)-D-Leu-Gly-L-Phe-D,L-(α-Me)-Leu-NH(Pr);
and the like.

The compounds of this invention are prepared by routine methods for peptide synthesis. It is possible, during the synthesis of certain of the compounds of this invention, that partial racemization can occur. However, the extent of racemization, should such occur, is not sufficient to seriously alter the analgesic activity of the compounds of this invention.

The methods for preparing the compounds of this invention involve the coupling of amino acids or peptide fragments by reaction of the carboxyl function of one with the amino function of another to produce an amide linkage. In order to effectively achieve coupling, it is desirable, first, that all reactive functionalities not participating directly in the reaction be inactivated by the use of appropriate blocking groups, and, secondly, that the carboxyl function which is to be coupled be appropriately activated to permit coupling to proceed. All of this involves a careful selection of both reaction sequence and reaction conditions as well as utilization of specific blocking groups so that the desired peptide product will be realized. Each of the amino acids which is employed to produce the compounds of this invention and which has the particularly selected protecting groups and/or activating functionalities is prepared by employing techniques well recognized in the peptide art.

Selected combinations of blocking groups are employed at each point of the total synthesis of the compounds of this invention. These particular combinations have been found to function most smoothly. Other combinations would operate in the synthesis of the compounds of this invention, although, perhaps, with a lesser degree of success. Thus, for example, benzyloxycarbonyl (CBz), t-butyloxycarbonyl (BOC), t-amyloxycarbonyl (AOC), p-methoxybenzyloxycarbonyl (MBOC), adamantyloxycarbonyl (AdOC), and isobornyloxycarbonyl can be variously employed as amino blocking groups in the synthesis of the compounds of this invention. Furthermore, benzyl (Bzl) generally is employed as the hydroxy-protecting group for the tyrosyl residue even though others, such as p-nitrobenzyl (PNB), p-methoxybenzyl (PMB), and the like, could well be employed.

The carboxyl blocking groups used in preparing the compounds of this invention can be any of the typical ester-forming groups, including, for example, methyl, ethyl, benzyl, p-nitrobenzyl, p-methoxybenzyl, 2,2,2-trichloroethyl, and the like.

Coupling of the suitably protected N-blocked amino acid or peptide fragment with a suitably protected carboxy-blocked amino acid or peptide fragment in preparation of the compounds of this invention consists of rendering the free carboxyl function of the amino acid or peptide fragment active to the coupling reaction. This can be accomplished using any of several well recognized techniques. One such activation technique involves conversion of the carboxyl function to a mixed anhydride. The free carboxyl function is activated by reaction with another acid, typically a derivative of carbonic acid, such as an acid chloride thereof. Examples of acid chlorides used to form mixed anhydrides are ethyl chloroformate, phenyl chloroformate, sec-butyl chloroformate, isobutyl chloroformate, pivaloyl chloride, and the like. Preferably, isobutyl chloroformate is employed.

Another method of activating the carboxyl function for the purpose of carrying out the coupling reaction is by conversion to its active ester derivative. Such active esters include, for example, a 2,4,5-trichlorophenyl ester, a pentachlorophenyl ester, a p-nitrophenyl ester, and the like. Another coupling method available for use is the well-recognized azide coupling method.

The preferred coupling method in preparation of the compounds of this invention involves the use of N,N'-dicyclohexylcarbodiimide (DCC) to activate the free carboxyl function thereby permitting coupling to proceed. This activation and coupling technique is carried out employing an equimolar quantity of DCC relative to the amino acid or peptide fragment and is carried out in the presence of an equimolar quantity of 1-hydroxybenzotriazole (HBT). The presence of HBT suppresses undesirable side reactions including the possibility of racemization.

Cleavage of selected blocking groups is necessary at particular points in the synthetic sequence employed in preparation of the compounds of this invention. A chemist of ordinary skill in the art of peptide synthesis can readily select from representative protecting groups those groups which are compatible in the sense that selective cleavage of the product can be accomplished permitting removal of one or more but less than all of the protecting groups present on the amino acid or peptide fragment. These techniques are well recognized in the peptide art. A fuller discussion of the techniques which are available for selective cleavage is provided in the literature in Schroder and Lubke, *The Peptides*, Volume I, Academic Press, New York, (1965), and especially in the Table provided at pages 72–75 thereof.

Cleavage of carboxyl protecting groups can be accomplished by alkaline saponification. Relatively strong alkaline conditions, typically using an alkali metal hydroxide, such as sodium hydroxide, potassium hydroxide, lithium hydroxide, and the like, are generally employed to deesterify the protected carboxyl. The reaction conditions under which saponification is accomplished are well recognized in the art. The carboxyl blocking groups also can be removed by catalytic hydrogenolysis including, for example, hydrogenolysis in the presence of a catalyst such as palladium on carbon. Furthermore, in those instances in which the carboxyl blocking group is p-nitrobenzyl or 2,2,2-tri-chloroethyl, deblocking can be accomplished by reduction in the presence of zinc and hydrochloric acid.

The amino blocking groups are cleaved by treating the protected amino acid or peptide with an acid such as formic acid, trifluoroacetic acid (TFA), p-toluenesulfonic acid (TSA), benzenesulfonic acid (BSA), naphthalenesulfonic acid, and the like, to form the respective acid addition salt product. Cleavage of the amino blocking group also can be accomplished by treating the blocked amino acid or peptide with a mixture of HBr or HCl and acetic acid to produce the corresponding hydrobromide or hydrochloride acid addition salt. The particular method or reagent which is employed will depend upon the chemical or physical characteristics of the materials involved in the specific deblocking reaction. The resulting acid addition salt can be converted to a more pharmaceutically acceptable form by treatment with a suitable ion exchange resin, such as DEAE Sephadex A25, Amberlyst A27, and the like.

The hydroxy-protecting group present on the tyrosyl residue can be retained on the peptide throughout the sequence of its preparation, being removed during the final synthetic step in conjunction with cleavage of the amino blocking group. However, depending upon the conditions employed for removal of the carboxyl blocking group, it may be removed earlier in the preparative sequence. When the carboxyl group is cleaved by alkaline saponification, the hydroxy-protecting group is retained; however, when catalytic hydrogenolysis is employed for removal of the carboxyl protecting group, the hydroxy protecting group also is cleaved. The latter situation does not represent a serious problem since preparation of the compounds of this invention can be accomplished in the presence of a tyrosyl residue having a free hydroxyl group.

A preferred specific method for preparing the compounds of this invention involves coupling a separately prepared N-terminal tripeptide with a separately prepared C-terminal dipeptide amide or the corresponding primary alcohol (in those instances in which Z is —CH$_2$OH) followed by appropriate deblocking of any remaining blocked moieties. Alternatively, the separately prepared C-terminal dipeptide or dipeptide-like moiety which is reacted with the N-terminal tripeptide can be structured so as to contain a group which represents a precursor to the desired C-terminal amide or primary alcohol. The general sequence, illustrating preparation of a pentapeptide of this invention, can be depicted as follows. In the sequence, the letter Z represents an amide or primary alcohol moiety, the symbol AA represents an amino acid residue, and the number appended to the symbol AA represents the position of the amino acid in the ultimate peptide product sequence.

amino acid moiety. Reaction techniques such as those described above are employed in this as well as any other contemplated preparative sequence.

In certain of the compounds of this invention, one or both of the groups $R_1$ and $R_2$ are $C_1$-$C_3$ primary alkyl. In these instances, the appropriate N-substituted tyrosine is employed in the preparative sequence. Any of the N-monosubstituted tyrosines can be prepared as follows using an N-protected tyrosine as starting material:

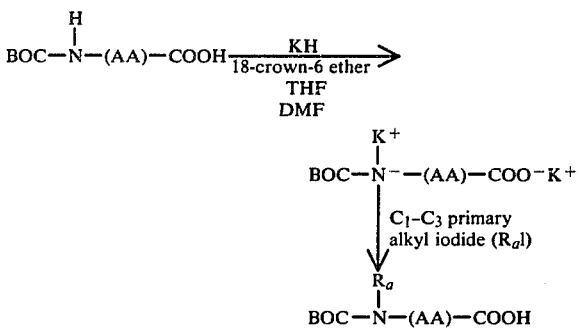

As the above sequence indicates, the tyrosine first is treated with potassium hydride in the presence of a suitable crown ether to generate the dianion. The intermediate then is treated with the appropriate alkyl iodide to obtain the desired N-substituted tyrosine.

It will be apparent to those of ordinary skill in the art of peptide synthesis that racemization at the α-carbon can occur under strongly alkaline conditions such as those employed in the above alkylation procedure. The degree of racemization may vary depending upon the particular amino acid which is involved. Racemization can be minimized by using excess alkylating agent and by keeping the reaction time as short as possible. Nevertheless, even in the event that excessive racemization does occur, the product can be purified by recrystallization as the salt of a suitable chiral amine, for example, as the salt of d(+) α-phenylethylamine.

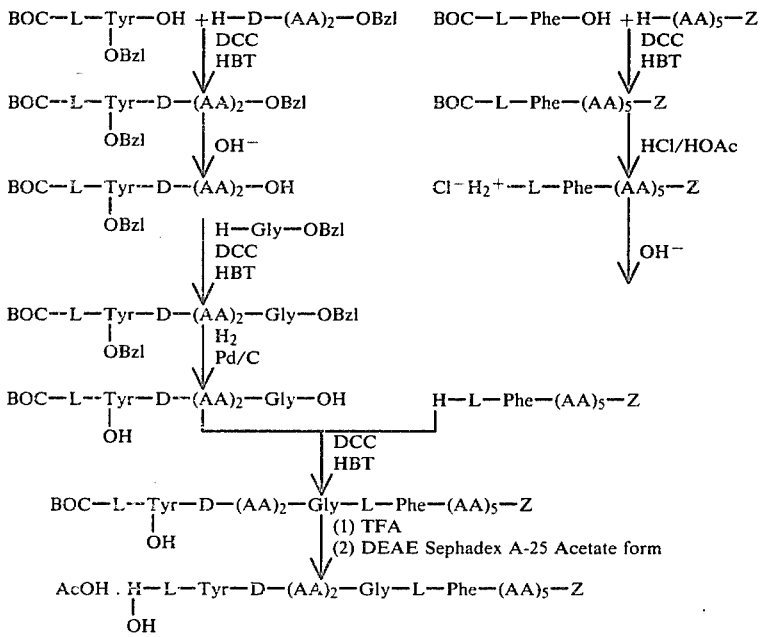

The above represents only one sequence for preparing compounds of this invention. Other sequences are available. Another method which can be employed involves the step-wise, sequential addition of single amino acids in construction of the peptide chain beginning with the carboxamide or primary alcohol terminal In the instances in which both $R_1$ and $R_2$ are the same $C_1$-$C_3$ primary alkyl, the desired N,N-disubstituted tyrosine can be prepared by the following sequence:

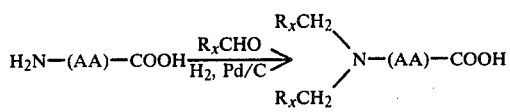

In the foregoing, $R_xCHO$ represents formaldehyde, acetaldehyde, or propionaldehyde.

In those instances in which $R_1$ and $R_2$ are different $C_1$-$C_3$ primary alkyl groups, the N,N-disubstituted tyrosine is available by treating the appropriate N-monosubstituted tyrosine, prepared in accordance with the foregoing sequence, with formaldehyde or acetaldehyde as described hereinabove.

The C-terminal portion of the peptides of this invention is derivatized to its primary alcohol or its amide. In the amide pentapeptides of this invention, the amide is unsubstituted or N-monosubstituted. Derivatization to the amide is accomplished by activation of the carboxyl group of the amino acid with N,N'-dicyclohexylcarbodiimide (DCC) in the presence of 1-hydroxybenzotriazole (HBT) to give the HBT ester. In producing the pentapeptides of this invention, the ester then is reacted with anhydrous ammonia or the appropriate primary amine to give the unsubstituted or N-monosubstituted amide. Suitable primary amines for preparation of the pentapeptides of this invention include methylamine, ethylamine, and n-propylamine.

Those compounds of this invention in which Y is acetyl are prepared from the corresponding N-blocked peptide in which Y is hydrogen. This latter compound is treated with acetic anhydride in the presence of pyridine to produce the corresponding N-blocked, O-acetyl peptide. Upon deblocking with a mixture of hydrochloric acid and acetic acid, the desired compound is obtained.

The compounds of this invention are valuable pharmaceutical agents. They exhibit analgesic activity and also neuroleptic activity. They are especially useful in alleviation of pain and amelioration of emotional disturbances when administered parenterally to mammals, including humans.

The compounds of this invention may be administered alone or in combination with pharmaceutically acceptable carriers, the proportion of which is determined by the solubility and chemical nature of the compound, the selected route of administration, and standard pharmaceutical practice.

Preferred compositions are those suitable for parenteral administration, that is, intramuscular, subcutaneous, or intravenous. These include sterile, injectable solutions or suspensions, and sterile injectable depot or slow-release formulations. Particularly convenient sterile, injectable solutions are made up in isotonic saline or isotonic dextrose. The sterile, injectable compositions can be prepared and stored as such or they can be prepared immediately prior to use by adding a sterile medium, for example, water, to a known weight of sterile ingredient enclosed in a vehicle, for example, a vial or an ampoule, which maintains sterility of the ingredient. The known weight of sterile ingredient may also contain sufficient sterile dextrose or sodium chloride to provide an isotonic solution or suspension after addition of the sterile medium.

Physicians will determine the particular dosage of the compounds of this invention which is most suitable. The selected dosages will vary depending upon the mode of administration, the particular compound administered, the patient under treatment, and the kind of treatment. In general, however, when the compound is administered for analgesic purposes, the dosage will range from about 1 to about 100 mg., and, preferably, from about 10 to about 40 mg., when administered intramuscularly or subcutaneously, and from about 0.1 to about 10 mg., and, preferably, from about 0.3 to about 3 mg., when administered intravenously.

When the compound is administered for neuroleptic purposes, the dosage generally will range from about 20 to about 200 mg., and preferably, from about 30 to about 100 mg., when administered intramuscularly or subcutaneously, and from about 2 to about 20 mg., and, preferably, from about 3 to about 10 mg., when administered intravenously.

The following examples are provided to illustrate the preparation and activity of the compounds of this invention. They are not intended to be limiting upon the scope thereof.

EXAMPLE 1

Preparation of L-Tyrosyl-D-alanyl-glycyl-L-phenylalanyl-D,L-α-methylmethionylamide, Hydrochloride salt.

A. Benzyl D-Alinate p-Toluenesulfonate.

To a mixture of 100 ml. of benzyl alcohol and 200 ml. of benzene containing 55.1 g. (0.29 mole) of p-toluenesulfonic acid monohydrate was added 25 g. (0.281 mole) of D-alanine. The mixture was brought to reflux, and water was removed azeotropically in a Dean-Stark apparatus. The mixture was heated for fifteen hours and then was cooled to room temperature and diluted with ether. The resulting precipitate was collected and recrystallized from methanolether to afford 55.3 g. (56%) of the title compound, m.p. 112°-115° C.

Analysis, calculated for $C_{17}H_{21}NO_5S$ (351.42): C, 58.10; H, 6.02; N, 3.99. Found: C, 58.19; H, 6.06; N, 3.82.

B. Benzyl N$^\alpha$-t-Butyloxycarbonyl-O-benzyl-L-tyrosyl-D-alinate.

To 200 ml. of dry N,N-dimethylformamide (DMF) was added 35.1 g. (0.1 mole) of the product from Part A. The resulting mixture was stirred and cooled to 0° C., and 11.2 g. (0.1 mole) of diazabicyclooctane (DABCO) was added. The mixture was stirred for ten minutes at 0° C., and 37.1 g. (0.1 mole) of N$^\alpha$-t-butyloxycarbonyl-O-benzyl-L-tyrosine was added followed by 13.5 g. (0.1 mole) of 1-hydroxybenzotriazole (HBT) and 20.6 g. (0.1 mole) of N,N'-dicyclohexylcarbodiimide (DCC). The resulting mixture was stirred at 0° C. for three hours and then at room temperature for twenty-four hours. The mixture then was cooled to 0° C., the resulting suspension was filtered, and the filtrate was concentrated in vacuo. The resulting residue then was redissolved in ethyl acetate and was washed successively with 1N NaHCO$_3$, water, 0.75 N cold citric acid, and water. The organic layer then was dried over magnesium sulfate, filtered, and concentrated in vacuo. The resulting residue then was dissolved in hot ethanol. Crystallization ensued upon cooling. After one recrystallization from ethanol, 41.5 g. (80%) of pure title compound was obtained, m.p. 121°-123° C.

Analysis, calculated for $C_{30}H_{36}N_2O_6$ (520.63): C, 69.21; H, 6.97; N, 5.38. Found: C, 68.99; H, 6.75; N, 5.17.

C. $N^\alpha$-t-Butyloxycarbonyl-O-benzyl-L-tyrosyl-D-alanine.

To a mixture of 200 ml. of tetrahydrofuran (THF) and 20 ml. of water was added 31.2 g. (0.06 mole) of the product from Part B. The resulting solution was cooled to 0° C., and 13.2 ml. (1.1 equiv.) of 5 N sodium hydroxide was added slowly. The resulting mixture was stirred and allowed slowly to warm to room temperature. After five hours, the mixture was partitioned between water and ether. The aqueous layer was separated and cooled, the pH was adjusted to 2 by addition of citric acid, and the mixture was extracted with ethyl acetate. The ethyl acetate extract was washed with water, dried over magnesium sulfate, filtered, and diluted with ether. The resulting precipitate was collected to afford 17.7 g (67%) of the title compound, m.p. 160°–162° C.

Analysis, calculated for $C_{24}H_{30}N_2O_6$ (442.51): C, 65.14; H, 6.83; N, 6.63. Found: C, 64.73; H, 6.70; N, 6.20.

D. Benzyl $N^\alpha$-t-Butyloxycarbonyl-O-benzyl-L-tyrosyl-D-alanyl-glycinate.

To 70 ml. of dry DMF was added 6.74 g. (0.02 mole) of the p-toluenesulfonic acid salt of benzyl glycinate. The resulting mixture was cooled to 0° C., and 2.24 g. (0.020 mole) of DABCO was added. The mixture was stirred for a few minutes, and 8.84 g. (0.020 mole) of the product of Part C was added followed by 2.7 g. (0.020 mole) of the HBT and 4.12 g. (0.020 mole) of DCC. The reaction mixture was stirred for two hours at 0° C. and then for twenty-four hours at room temperature. The resulting suspension was cooled to 0° C., filtered, and the filtrate was concentrated in vacuo. The resulting residue was dissolved in ethyl acetate and was washed successively with 1 N sodium bicarbonate, water, cold 0.75 N citric acid, and water. The organic phase was dried over magnesium sulfate, filtered, and concentrated in vacuo. The resulting residue was crystallized from ethanol to give 10.8 g. (92%) of pure title compound, m.p. 145°–147° C.

Analysis, calculated for $C_{33}H_{39}N_3O_7$ (589.69): C, 67.22; H, 6.67; N, 7.13. Found: C, 67.32; H, 6.83; N, 6.91.

E. $N^\alpha$-t-Butyloxycarbonyl-L-tyrosyl-D-alanyl-glycine.

To 60 ml. of DMF was added 10.5 g. (0.018 mole) of the product from Part D followed by 2.5 g. of 5% Pd/C added as a DMF slurry. The resulting mixture was flushed with nitrogen, and hydrogen was introduced via a gas dispersion tube at atmospheric pressure and room temperature. After 3.5 hours, the hydrogen flow was terminated, and the catalyst was removed by filtration. The filtrate was concentrated in vacuo. Trituration of the residue with ether gave 5.4 g. (75%) of the title compound as amorphous solid.

Analysis, calculated for $C_{26}H_{26}N_2O_5$ (446.65): C, 69.94; H, 5.87; N, 6.27. Found: C, 70.08; H, 5.82; N, 6.16.

F. $N^\alpha$-t-Butyloxycarbonyl-D,L-$\alpha$-methylmethionine.

To 160 ml. of N,N-dimethylformamide (DMF) were added 10 g. (0.061 mole) D,L-$\alpha$-methylmethionine. The resulting mixture was stirred at room temperature, and 8.1 ml. (0.061 mole) of 1,1,3,3-tetramethylguanidine and 12 ml. (0.061 mole) of dicyclohexylamine were added. To the mixture were added dropwise over a thirty minute period 12.34 ml. (1.5 equiv.) of t-butyloxycarbonyl azide in 20 ml. of DMF. The reaction mixture then was stirred at room temperature for two hours, at 60° C. for twenty-four hours, and at 100° C. for twenty-four hours. The reaction mixture was cooled to room temperature, and the resulting dicyclohexylamine azide was filtered. The filtrate was concentrated in vacuo. The resulting residue was dissolved in 1 N sodium hydroxide, and the solution was extracted with ether. The aqueous layer was separated and acidified to pH 2.0 with 2 N HCl. The aqueous mixture then was extracted with ethyl acetate. The ethyl acetate was washed with water, dried over magnesium sulfate, and concentrated in vacuo. The resulting oil was dried to give 7.8 g. of crude title compound. The crude oil was dissolved in chloroform and applied to a 2×10 cm. column containing Grace and Davison Grade 62 silica gel. The column was eluted with a step gradient from 100% chloroform to a 95:5 mixture of chloroform and methanol. Fractions were combined according to thin-layer chromatography (TLC) profile. Upon evaporation of solvent, 4.7 g. (30%) of the title compound were obtained.

NMR $\delta$ 2.1 (—S—CH$_3$), 1.55 ($\alpha$-methyl), and 1.4 Hz (Boc).

G. $N^\alpha$-t-Butyloxycarbonyl-D,L-$\alpha$-methylmethionine amide.

The product from Part F was dissolved in 40 ml. of DMF. The mixture was cooled to −15° C., and 2.58 ml. (1.1 equiv.) of isobutyl chloroformate were added followed by 2.16 ml. (1.0 equiv.) of N-methylmorpholine. The resulting mixture was stirred for 10 minutes at −15° C., and anhydrous ammonia was bubbled into the mixture for 30 minutes. The mixture was stirred for 3 hours at −15° C., and then was poured into a beaker containing 200 ml. of ice. The resulting aqueous mixture was extracted with ether. The organic layer was separated and washed successively with 1.5 N citric acid, water, 1 N sodium bicarbonate, and water. The ether solution then was dried over magnesium sulfate and evaporated in vacuo to give a syrup. The syrup was crystallized from a mixture of ether and petroleum ether to give 1.2 g. (26%) of title compound, m.p. 120°–124° C.

Analysis, calculated for $C_{11}H_{22}N_2O_3S$ (262.37): C, 50.36; H, 8.45; N, 10.68. Found: C, 50.63; H, 8.18; N, 10.69.

H. $N^\alpha$-t-Butyloxycarbonyl-L-phenylalanine-D,L-$\alpha$-methylmethionine amide.

To a mixture of 20 ml. of glacial acetic acid, 2 ml. of anisole, and 2 ml. of triethylsilane were added 1.1 g. (4.2 millimoles) of the product from Part G. Gaseous hydrogen chloride was bubbled into the reaction mixture for 20 minutes. The mixture then was poured into ether, and the resulting precipitate was collected and dried (830 mg.). The collected hydrochloride was dissolved in 20 ml. of DMF. The solution was cooled to 0° C., and 0.84 ml. (4.2 millimoles) of dicyclohexylamine was added. The mixture was stirred for a few minutes, and 570 mg. (4.2 millimoles) of HBT, 1.1 g. (4.2 millimoles) of $N^\alpha$-t-butyloxycarbonyl-L-phenylalanine, and 870 mg. (4.2 millimoles) of DCC were added. The resulting mixture was stirred at 0° C. for 2 hours and then at room temperature for 24 hours. The mixture was cooled to 0° C. and filtered. The filtrate was concentrated in vacuo in oil. The oil was dissolved in ethyl acetate, and the ethyl acetate solution was washed successively with 1

N sodium bicarbonate, water, cold 0.75 N citric acid, and water. The organic layer then was dried over magnesium sulfate and concentrated in vacuo to an oil. The oil was crystallized from a mixture of methanol, ether, and petroleum ether to give 1.7 g. (81%) of title compound, m.p. 179°–184° C. $[\alpha]_D^{25}$ −3.2° (c=0.5 in methanol).

Analysis, calculated for $C_{20}H_{31}N_3O_4S$ (409.5): C, 58.65; H, 7.63; N, 10.26. Found: C, 58.85; H, 7.36; N, 10.02.

I.

$N^\alpha$-t-Butyloxycarbonyl-L-tyrosyl-D-alanyl-glycyl-L-phenylalanyl-D,L-α-methylmethionine amide.

To 10 ml. glacial acetic acid containing 1 ml. of anisole and 1 ml. of triethylsilane were added 1.3 g. (3.2 millimole) of the product from Part H. Gaseous hydrogen chloride was bubbled into the reaction mixture for 25 minutes. The reaction mixture then was poured into ether, and the resulting precipitate was collected and dried (900 mg.). The collected hydrochloride then was dissolved in 20 ml. of DMF, and 1.89 g. (3.2 millimole) of the dicyclohexylamine salt of the product from Part E were added to the reaction mixture. The mixture was stirred for a few minutes and then was cooled to 0° C., and 432 mg. (3.2 millimoles) of HBT and 660 mg. (38.2 millimoles) of DCC were added. The mixture was stirred at 0° C. for 2 hours and then at 4° C. for 24 hours. The mixture then was cooled to 0° C. and filtered. The filtrate was concentrated in vacuo to an oil which was dissolved in ethyl acetate. The ethyl acetate solution was extracted successively with 1 N sodium bicarbonate, water, cold 0.75 N citric acid, and water. The organic phase was then dried over magnesium sulfate and concentrated in vacuo to obtain an oil. The oil was crystallized from hot ethyl acetate to give 800 mg. (36%) of the title compound. $[\alpha]_D^{25}$ +16.5° (c=0.5 in methanol).

Analysis, calculated for $C_{34}H_{48}N_6O_8S$ (700.86): C, 58.27; H, 6.80: N, 11.99. Found: C, 58.53: H, 6.99: N, 11.85.

Amino acid analysis: Gly, 1.77; Ala, 1.76; Tyr, 1.76; Phe, 1.53; NH₃, 1.63.

J.

L-Tyrosyl-D-alanyl-glycyl-L-phenylalanyl-D,L-α-methylmethionine amide hydrochloride.

To 10 ml. of glacial acetic acid containing 1 ml. of anisole were added 700 mg. (1 millimole) of the product from Part I. Gaseous hydrogen chloride was bubbled into the reaction mixture for 20 minutes. The mixture was freeze dried to give 630 mg. (99%) of the title compound. $[\alpha]_D^{25}$ +48.9 (c=0.3 in 1 N HCl).

Amino acid analysis: Tyr, 1.04; Ala, 1.04; Gly, 1.04; Phe, 0.75; NH₃, 0.96.

EXAMPLE 2

Preparation of L-Tyrosyl-D-alanyl-glycyl-L-phenylalanyl-D,L-α-methylleucine Amide, Hydrochloride Salt.

A. Methyl D,L-α-methylleucine hydrochloride.

To 100 ml. of methyl alcohol containing 20.4 ml. (0.42 mole) of benzaldehyde were added 36.4 g. (0.2 mole) of L-leucine, methyl ester hydrochloride. The mixture was stirred at room temperature, and 20 g. of anhydrous magnesium sulfate were added. The mixture then was cooled to 0° C., and 27.8 ml. (0.2 mole) of triethylamine in 40 ml. of ether were added dropwise over a one hour period. The resulting mixture was stirred at 0° C. for one hour and then at room temperature for 24 hours. The mixture then was diluted with 8 volumes of ether and filtered. The filtrate was concentrated in vacuo to obtain 40.8 g. of an oil. NMR δ 0.9 (isopropyl methyls), 3.7 (—CO₂CH₃), and 8.3 Hz (PhC$\underline{H}$=N—).

A suspension of 0.17 mole of potassium hydride in 100 ml. of dry tetrahydrofuran (THF) containing 1 g. of 18-crown-6 ether was prepared. The suspension was stirred at room temperature, and a solution of 39.6 g. (0.17 mole) of the Schiff base of leucine, methyl ester, dissolved in 50 ml. of THF was added dropwise over a 30 minute period. A solution of 10.6 ml. (0.17 mole) of methyl iodide in 30 ml. of THF was added dropwise over a 15 minute period. Stirring was continued for 3 hours, and 5 ml. of glacial acetic acid were added. The mixture was stirred an additional 10 minutes, and was poured into 400 ml. of ice. The aqueous phase was separated and extracted with ether. The ether layer was washed successively with 0.75 N citric acid, water, 1 N sodium bicarbonate, and water. The ether layer was dried over magnesium sulfate and concentrated in vacuo to an oil. The oil was stirred in 80 ml. of 1 N HCl at room temperature for one hour. Ether was added to the mixture, and the aqueous layer was separated. Concentrated HCl (17 ml.) was added to the aqueous phase, and the mixture was refluxed for 15 hours. The mixture was cooled to room temperature, and the pH was adjusted to 7.0 with 2 N sodium hydroxide. The aqueous mixture was treated with carbon and filtered. The filtrate was concentrated in vacuo to a solid which was dried. The solid was suspended in anhydrous methanol, and 12.3 ml. (0.17 mole) of thionyl chloride were added dropwise to the mixture. The mixture was stirred for 24 hours at room temperature, and an additional 20 ml. of thionyl chloride were added dropwise. The mixture then was refluxed for 6 hours and stirred for 48 hours at room temperature. The resulting precipitate was filtered, and the filtrate was concentrated in vacuo to obtain 9 g. (23%) of the title compound as an oil.

NMR δ 3.8 (—CO₂CH₃), 1.5 (α-methyl), and 0.9 Hz (isopropyl methyls).

B.

$N^\alpha$-t-Butyloxycarbonyl-L-phenylalanine-D,L-α-methylleucine, methyl ester.

To 80 ml. of DMF were added 9 g. (45.9 millimoles) of the product from Part A. The mixture was cooled to 0° C., and 6.4 ml. (45.9 millimoles) of triethylamine were added. The mixture was stirred at 0° C. for a few minutes, and then 11.8 g. (45.9 millimoles) of $N^\alpha$-t-butyloxycarbonyl-L-phenylalanine, 6.2 g. (45.9 millimoles) of HBT, and 9.5 g. (45.9 millimoles) of DCC were added. The mixture was stirred at 0° C. for two hours and at room temperature for 48 hours. The mixture was cooled to 0° C., filtered, and the filtrate was evaporated in vacuo. The residue was dissolved in ethyl acetate, and the ethyl acetate solution was extracted successively with 1 N sodium bicarbonate, water, 0.75 N cold citric acid, and water. The organic phase was dried over magnesium sulfate and evaporated in vacuo to an oil. The oil then was dissolved in chloroform and added to a 10×2 cm. column containing Grace and Davison grade 62 silica gel. The column was eluted with a step gradient of 100% chloroform to a 95:5 mixture of chloroform and methanol. The collected fractions were combined according to the TLC profile. Upon evaporation of the solvent, 17 g. (94%) of the title compound were obtained as an oil. $[\alpha]_D^{25} -7.9°$ (c=0.5 in methanol).

NMR δ 7.2 (phenyl), 3.65 (—CO$_2$CH$_3$), 3.0 (PhCH$_2$—), and 1.4 Hz. (BOC).

C.
N$^\alpha$-t-Butyloxycarbonyl-L-phenylalanine-D,L-α-methylleucine amide.

To 80 ml. of methanol were added 16 g. (40.1 millimoles) of the product from Part B. The mixture was placed in a pressure bottle. The pressure bottle was cooled to −78° C., 30 ml. of anhydrous ammonia were added, and the bottle was sealed. The mixture was stirred at room temperature for 72 hours. The pressure bottle was cooled, opened, and the ammonia was allowed to evaporate. The resulting mixture was concentrated in vacuo, and the remaining oil was crystallized from ether to give 4.3 g. (27%) of the title compound. $[\alpha]_D^{25} -11.1°$ (c=0.5 in methanol).

Analysis, calculated for C$_{21}$H$_{33}$N$_3$O$_4$ (391.5): C, 64.42; H, 8.50; N, 10.73. Found: C, 64.19; H, 8.22; N, 10.54.

D.
N$^\alpha$-t-Butyloxycarbonyl-L-tyrosyl-D-alanyl-glycyl-L-phenylalanyl-D,L-α-methylleucine amide.

To 30 ml. of a 1.5 N solution of HCl in glacial acetic acid containing 2.5 ml. of anisole were added 3.92 g. (10 millimoles) of the product from Part C. The mixture was stirred at room temperature for 30 minutes. The mixture was poured into ether, and the precipitate was collected and dried (3.2 g.). The hydrochloride salt was dissolved in 60 ml. of DMF. The solution was cooled to 0° C., and 5.9 g. (10 millimoles) of N$^\alpha$-t-butyloxycarbonyl-L-tyrosyl-D-alanylglycine, dicyclohexylamine salt (prepared as in Example 1) were added. The reaction mixture was stirred at 0° C. for a few minutes, and 1.35 g. (10 millimoles) of HBT and 2.06 g. (10 millimoles) of DCC were added. The mixture was stirred at 0° C. for 2 hours and at 4° C. for 24 hours after which it was cooled to 0° C. and filtered. The filtrate was concentrated in vacuo to an oil. The oil was dissolved in ethyl acetate, and the ethyl acetate solution was extracted successively with 1 N sodium bicarbonate, water, cold 0.75 N citric acid, and water. The solution was dried over magnesium sulfate and concentrated in vacuo to an oil. A solution of the oil in chloroform was added to a 40×3 cm. column containing Grace and Davison grade 62 silica gel. The product was eluted with a step gradient of 100% chloroform to a 90:10 mixture of chloroform and methanol. The product was isolated according to the TLC profile of the fractions collected to give 2.4 g. (34%) of the title compound. $[\alpha]_D^{25} +18.4°$ (c=0.5 in methanol).

Analysis, calculated for C$_{35}$H$_{50}$N$_6$O$_8$ (682.8): C, 61.57; H, 7.38; N, 12.31. Found: C, 61.51; H, 7.15; N, 12.53.

E.
L-Tyrosyl-D-alanyl-glycyl-L-phenylalanyl-D,L-α-methylleucine amide hydrochloride.

To 30 ml. of a solution of 2 N HCl in glacial acetic acid containing 2 ml. of anisole were added 2.1 g. (3.1 millimoles) of the product from Part D. The mixture was stirred at room temperature for 30 minutes. The mixture was poured into ether, and the resulting precipitate was collected and dried to give 1.7 g. (89%) of title compound. $[\alpha]_D^{25} +75.3°$ (c=0.5 in 1 N HCl).

Amino acid analysis: Tyr, 1.03; Ala, 1.03; Gly, 1.03; Phe, 1.01; NH$_3$, 0.89.

EXAMPLE 3

Preparation of L-Tyrosyl-D-alanyl-glyciyl-L-phenylalanyl-D,L-α-methylmethionine Carbinol, Acetate Salt.

A. D,L-α-Methylmethionine, methyl ester hydrochloride.

To 100 ml. of anhydrous methanol were added 10 g. (0.061 moles) of D,L-α-methylmethionine. The mixture was stirred at room temperature, and 9 ml. (0.123 mole) of thionyl chloride were added dropwise over a 30 minute period. The mixture was stirred at room temperature for 48 hours and at reflux for 24 hours. The mixture was cooled to room temperature and diluted with 8 volumes of ether. The ether was decanted from an oil. The oil was dissolved in a minimum of methanol, and the mixture was filtered. The filtrate was concentrated in vacuo to afford 6 g. (46%) of the title compound as a solid.

NMR δ 3.9 (—CO$_2$CH$_3$), 2.1 (—S—CH$_3$), and 1.7 Hz. (α-methyl).

B.
N$^\alpha$-t-Butyloxycarbonyl-L-phenylalanyl-D,L-α-methylmethionine, methyl ester.

To 50 ml. of DMF were added 6 g. (0.28 mole) of the product from Part A. The mixture was cooled to 0° C., and 3.9 ml. (0.028 mole) of triethylamine were added. The mixture was stirred at 0° C. for a few minutes, and 7.43 g. (0.028 mole) of N$^\alpha$-t-butyloxycarbonyl-L-phenylalanine, 3.8 g. (0.028 mole) of HBT, and 5.77 g. (0.028 mole) of DCC were added. The mixture was stirred at 0° C. for 2 hours and at room temperature for 24 hours. The mixture was cooled to 0° C., the precipitate was removed by filtration, and the filtrate was evaporated in vacuo. The residue was dissolved in ethyl acetate, and the ethyl acetate solution was extracted successively with 1 N sodium bicarbonate, water, 0.75 N cold citric acid, and water. The organic phase was dried over magnesium sulfate and evaporated in vacuo to an oil. The oil was dissolved in chloroform, and the chloroform solution was placed on a 10×2 cm. column containing Grace and Davison grade 62 silica gel. The column was eluted with a step gradient of 100% chloroform to a 95:5 mixture of chloroform and methanol. The fractions were combined according to the TLC profile. Upon evaporation of solvent, 6.0 g. (51%) of the title compound were obtained as an oil. $[\alpha]_D^{25} -6.4°$ (c=0.6 in methanol).

NMR δ 7.25 (phenyl), 3.7 (—CO$_2$CH$_3$), 2.0 (—S—CH$_3$), 1.5 (α-methyl), and 1.45 Hz. (t-butyl).

C.
N$^\alpha$-t-Butyloxycarbonyl-L-phenylalanyl-D,L-α-methylmethionine carbinol.

To a solution of 1.82 g. (0.048 mole) of sodium borohydride in 125 ml. of 80% ethanol was added over a 15 minute period at 0° C. a solution of 3.4 g. (0.008 mole) of the product from Part B in 200 ml. of 80% ethanol. Lithium chloride (2.08 g.; 0.048 mole) in 100 ml. of 80% ethanol were added to the mixture over a 15 minute period at 0° C. The resulting mixture was stirred for 18 hours at room temperature, and the mixture was adjusted to pH 2 by addition of 1 N HCl with cooling. The mixture was adjusted to pH 6 by addition of saturated aqueous sodium bicarbonate after which it was concentrated under reduced pressure. Water (200 ml.) was added to the residue. The aqueous solution then was extracted with ethyl acetate, and the ethyl acetate extract was washed successively with water, 0.75 N citric acid, and water. The mixture was dried over magnesium sulfate and concentrated in vacuo to obtain 3.0 g. (94%) of the title compound as an oil. $[\alpha]_{365}^{25}$ +6.4° (c=0.5 in methanol).

NMR δ 7.3 (phenyl), 2.0 (—S—CH$_3$), 1.4 (t-butyl), and 1.1 Hz (α-methyl).

Analysis, calculated for $C_{20}H_{32}N_2O_4S$ (396.6): C, 60.58; H, 8.13; N, 7.06. Found: C, 60.35; H, 7.93; N, 6.83.

D.

N$^\alpha$-t-Butyloxycarbonyl-L-tyrosyl-D-alanyl-glycyl-L-phenylalanyl-D,L-α-methylmethionine carbinol.

To 20 ml. of trifluoroacetic acid containing 1 ml. of thioanisole and 1 ml. of triethylsilane were added 2.5 g. (6.3 millimoles) of the product from Part C. The mixture was stirred at 0° C. for 40 minutes. The mixture was poured into a mixture of ether and petroleum ether. The supernate portion was decanted, and the remaining oil was dried to an amorphous solid (2.1 g.).

To 50 ml. of DMF were added 1.18 g. (2 millimoles) of N$^\alpha$-t-butyloxycarbonyl-L-tyrosyl-D-alanyl-glycine, dicyclohexylamine salt (prepared as in Example 1). The solution was cooled to −15° C., and 0.26 ml. (2 millimoles) of isobutyl chloroformate was added rapidly to the stirring, cooled solution. The solution was stirred at −15° C. while the following was prepared.

To 5 ml. of DMF were added 820 mg. (2 millimoles) of the above amorphous solid. The solution was cooled to 0° C., and 0.22 ml. (2 millimoles) of N-methylmorphine was added in one portion. The solution was agitated to ensure complete reaction. The resulting mixture then was rapidly added to the above-prepared solution, and the total was stirred for three hours at −15° C. The mixture was poured onto a mixture of crushed ice and 1 N aqueous sodium bicarbonate. The aqueous mixture was extracted with ethyl acetate. The ethyl acetate was separated and washed successively with water, 0.75 N citric acid, and water. The ethyl acetate was dried over magnesium sulfate, and concentrated in vacuo to an oil. The oil was dissolved in chloroform, and the chloroform solution was applied to two EM Reagents preparative TLC plates. The TLC plates were eluted with a 9:1 mixture of chloroform and methanol. The major component was isolated to obtain 640 mg. (46%) of the title compound. $[\alpha]_D^{25}$ +11.0 (c=0.5 in methanol).

Analysis, calculated for $C_{34}H_{49}N_5O_8S$ (687.9): C, 59.37; H, 7.18; N, 10.18. Found: C, 59.24; H, 6.89; N, 10.07.

Amino acid analysis: Tyr, 1.02; Ala, 0.99; Gly, 0.99; Phe, 0.99.

E.

L-Tyrosyl-D-alanyl-glycyl-L-phenylalanyl-D,L-α-methylmethionine carbinol, acetate salt.

To 5 ml. of trifloroacetic acid containing 0.5 ml. of thioanisole were added 540 mg. (0.78 millimole) of the product from Part D. The mixture was stirred at 0° C. for 30 minutes. The mixture was freeze dried, and the freeze dried solid was dissolved in sufficient buffer (1% pyridine:0.05% acetic acid) to make 10 ml. The resulting solution was applied to a 2.5×99 cm. column of DEAE-Sephadex A-25 (acetate) previously equilibrated with the same buffer. The eluate was monitored at 280 nm, and the appropriate fractions were combined and lyophilized. Re-lyophilization from dilute acetic acid gave 356 mg. (70%) of the title compound as a white solid. $[\alpha]_D^{25}$ +55.7° (c=0.5 in 1 N HCl).

Analysis, calculated for $C_{31}H_{45}N_5O_8S$ (647.8): C, 57.48; H, 7.00; N, 10.81. Found: C, 57.70; H, 6.94; N, 10.62.

Amino acid analysis: Tyr, 1.00; Ala, 1.01; Gly, 0.99; Phe, 0.91.

The compounds of this invention are useful as analgesics. The analgesic activity of the compounds of this invention is demonstrated by the mouse hot plate test. In this test, a mouse is placed inside an upright acrylic cylinder comprising, as its base, a hot plate surface which is maintained at 52° C. The mouse is given, by subcutaneous injection, a predetermined amount of test compound dissolved or suspended in a suitable carrier, and, 15 minutes after administration of the test compound, the mouse is placed on the hot plate surface. The latencies in seconds until the occurrence of each of two separate phenomena then are recorded. First the latency until the mouse licks its hind paw is measured, and, secondly, the latency until the mouse jumps from the hot plate surface is measured. An agent which exhibits analgesic activity produces an increase in these latencies over those of control mice which receive injections only of the carrier. This must occur in a dose range which produces no motor incoordination or incapacitation. The following Table records the results obtained from this test, reflected in terms of increase over saline control. Each data point was determined using ten treated and ten control mice, and each represents the difference in mean response latency between treated and control animals. The mean control latency for the hind paw lick response was 28.4±0.9 seconds determined from eight groups of ten control mice each. The mean control jump latency was 52.4±3.7 seconds for studies run in the a.m. and 75.9±6.0 seconds for studies run in the p.m. as determined from four groups of ten mice each in the a.m. and four groups of ten mice each in the p.m.

TABLE
Analgesic Activity
Latency, Increase in Seconds over Control

| Compound[a] | Test[b] | Dose, mg/kg.[c] | | | | | |
|---|---|---|---|---|---|---|---|
| | | 0.1 | 0.3 | 1 | 3 | 10 | 30 |
| A | HPL | — | — | — | 5.9 | 15.3[1] | 15.9[3] |
| | EJ | — | — | — | 44.1[2] | 71.5[2] | 114.8[4] |
| B | HPL | — | — | 8.8[1] | 7.2 | 11.5[1] | 112.8[3] |
| | EJ | — | — | 39.8[1] | 88.3[4] | 122.8[4] | 182.6[4] |
| C | HPL | −2.6 | 1.7 | 8.3[1] | 11.2[2] | 18.8[4] | 10.6[1] |
| | EJ | 16.4 | 47.7[2] | 55.2[4] | 74.9[4] | 90.7[4] | 93.8[4] |

Footnotes:
[a]The designations refer to the following compounds:
A. L-Tyrosyl-D-alanyl-glycyl-L-phenylalanyl-D,L-α-methylmethionylamide, hydrochloride salt.
B. L-Tyrosyl-D-alanyl-glycyl-L-phenylalanyl-D,L-α-methylleucylamide, hydrochloride salt.
C. L-Tyrosyl-D-alanyl-glycyl-L-phenylalanyl-D,L-α-methylmethionine carbinol, acetate salt.
[b]The designations refer to:
HPL — hind paw lick.
EJ — escape jump.
[c]The numerals "1", "2", "3", and "4" appearing as superscripts indicate that the result is significant to $P < 0.05$, to $P < 0.01$, to $P < 0.001$, and to $P < 0.0001$, respectively.

We claim:
1. A compound of the formula

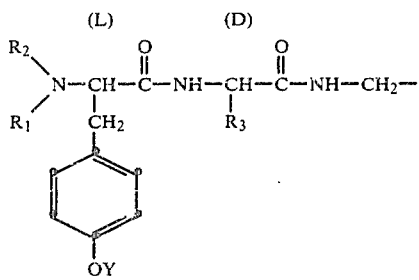

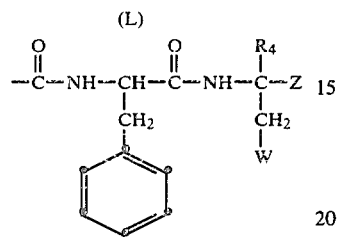

and pharmaceutically acceptable non-toxic acid addition salts thereof, in which L and D define the chirality;

$R_1$ and $R_2$ independently are hydrogen or $C_1$–$C_3$ primary alkyl;

$R_3$ is $C_1$–$C_4$ primary or secondary alkyl, $C_1$–$C_2$ hydroxyalkyl, or —$CH_2CH_2$—U—$CH_3$, in which U is O or S;

$R_4$ is $C_1$–$C_3$ primary alkyl;

Y is hydrogen or acetyl;

Z is —$CH_2OH$ or

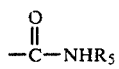

in which $R_5$ is $C_1$–$C_3$ alkyl or hydrogen; and W is isopropyl, —$VR_6$, or —$CH_2$—X—$CH_3$, in which V is O or S, $R_6$ is $C_1$–$C_4$ alkyl or aralkyl, and X is O, S, or —$CH_2$—.

2. Compound of claim 1, in which the moiety

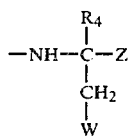

is present as the D,L-racemate.

3. Compound of claim 2, in which Y is hydrogen.
4. Compound of claim 2, in which $R_1$ and $R_2$ are hydrogen.
5. Compound of claim 2, in which $R_3$ is $C_1$–$C_4$ primary or secondary alkyl.
6. Compound of claim 5, in which $R_3$ is $C_1$–$C_4$ primary alkyl.
7. Compound of claim 2, in which $R_3$ is $C_1$–$C_2$ hydroxyalkyl.
8. Compound of claim 2, in which $R_3$ is —$CH_2CH_2$—U—$CH_3$.
9. Compound of claim 2, in which $R_4$ is methyl.
10. Compound of claim 2, in which $R_4$ is ethyl.
11. Compound of claim 2, in which $R_4$ is n-propyl.
12. Compound of claim 2, in which Z is

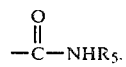

13. Compound of claim 2, in which Z is —$CH_2OH$.
14. Compound of claim 2, in which W is isopropyl.
15. Compound of claim 2, in which W is —$VR_6$.
16. Compound of claim 2, in which W is —$CH_2$—X—$CH_3$.
17. Compound of claim 12, in which $R_5$ is hydrogen.
18. Compound of claim 17, in which Y is hydrogen.
19. Compound of claim 18, in which $R_1$ and $R_2$ are hydrogen.
20. Compound of claim 19, in which $R_3$ is $C_1$–$C_4$ primary or secondary alkyl.
21. Compound of claim 20, in which $R_3$ is $C_1$–$C_4$ primary alkyl.
22. Compound of claim 19, in which $R_3$ is $C_1$–$C_2$ hydroxyalkyl.
23. Compound of claim 19, in which $R_3$ is —$CH_2CH_2$—U—$CH_3$.
24. Compound of claim 20, in which W is isopropyl.
25. Compound of claim 20, in which W is —$VR_6$.
26. Compound of claim 20, in which W is —$CH_2$—X—$CH_3$.
27. Compound of claim 26, in which X is sulfur.
28. Compound of claim 27, in which $R_3$ is $C_1$–$C_4$ primary alkyl.
29. Compound of claim 28, in which $R_4$ is methyl.
30. Compound of claim 29, in which $R_3$ is methyl.
31. Compound of claim 28, in which $R_4$ is ethyl.
32. Compound of claim 31, in which $R_3$ is methyl.
33. Compound of claim 28, in which $R_4$ is n-propyl.
34. Compound of claim 33, in which $R_3$ is methyl.
35. Compound of claim 24, in which $R_3$ is $C_1$–$C_4$ primary alkyl.
36. Compound of claim 35, in which $R_4$ is methyl.
37. Compound of claim 36, in which $R_3$ is methyl.
38. Compound of claim 35, in which $R_4$ is ethyl.
39. Compound of claim 38, in which $R_3$ is methyl.
40. Compound of claim 35, in which $R_4$ is n-propyl.
41. Compound of claim 40, in which $R_3$ is methyl.
42. Compound of claim 13, in which Y is hydrogen.
43. Compound of claim 42, in which $R_1$ and $R_2$ are hydrogen.
44. Compound of claim 43, in which $R_3$ is $C_1$–$C_4$ primary or secondary alkyl.
45. Compound of claim 44, in which $R_3$ is $C_1$–$C_4$ primary alkyl.
46. Compound of claim 43, in which $R_3$ is $C_1$–$C_2$ hydroxyalkyl.
47. Compound of claim 43, in which $R_3$ is —$CH_2CH_2$—U—$CH_3$.
48. Compound of claim 44, in which W is isopropyl.
49. Compound of claim 44, in which W is —$VR_6$.
50. Compound of claim 44, in which W is —$CH_2$—X—$CH_3$.
51. Compound of claim 50, in which X is sulfur.
52. Compound of claim 51, in which $R_3$ is $C_1$–$C_4$ primary alkyl.
53. Compound of claim 52, in which $R_4$ is methyl.
54. Compound of claim 53, in which $R_3$ is methyl.
55. Compound of claim 52, in which $R_4$ is ethyl.
56. Compound of claim 55, in which $R_3$ is methyl.
57. Compound of claim 52, in which $R_4$ is n-propyl.
58. Compound of claim 57, in which $R_3$ is methyl.
59. Compound of claim 48, in which $R_3$ is $C_1$–$C_4$ primary alkyl.
60. Compound of claim 59, in which $R_4$ is methyl.
61. Compound of claim 60, in which $R_3$ is methyl.
62. Compound of claim 59, in which $R_4$ is ethyl.
63. Compound of claim 62, in which $R_3$ is methyl.
64. Compound of claim 59, in which $R_4$ is n-propyl.
65. Compound of claim 64, in which $R_3$ is methyl.

* * * * *